United States Patent [19]
Waschkies

[11] Patent Number: 5,920,014
[45] Date of Patent: Jul. 6, 1999

[54] PROCESS FOR ASSESSING WELDED JOINTS

[75] Inventor: Eckhard Waschkies, Blieskastel, Germany

[73] Assignee: Fraunhofer -Gesellschaft Zur Forderung der Angewandten Forschung e.v., Munich, Germany

[21] Appl. No.: 08/374,646

[22] PCT Filed: Aug. 2, 1993

[86] PCT No.: PCT/DE93/00675

§ 371 Date: Jan. 31, 1995

§ 102(e) Date: Jan. 31, 1995

[87] PCT Pub. No.: WO94/03799

PCT Pub. Date: Feb. 17, 1994

[30] Foreign Application Priority Data

Jul. 31, 1992 [DE] Germany ............................ 42 25 251

[51] Int. Cl.[6] .................................................. G01N 29/04
[52] U.S. Cl. .............................................. 73/597; 73/602
[58] Field of Search .................................... 364/506, 507,
364/508; 376/252, 245; 976/DIG. 232;
73/597, 598, 602, 618, DIG. 1, 627; 219/109

[56] References Cited

U.S. PATENT DOCUMENTS

| | | | |
|---|---|---|---|
| 3,726,130 | 4/1973 | Hurlebaus | 73/629 |
| 4,099,045 | 7/1978 | Okuda | 73/629 |
| 4,265,119 | 5/1981 | Dubetz | 73/612 |
| 4,449,029 | 5/1984 | Nied | 73/598 |
| 5,063,779 | 11/1991 | Landry | 73/622 |

OTHER PUBLICATIONS

McMaster, R. C. *Nondestructive Testing Handbook*. N.Y., The Ronald Press Company, 1959. pp. 43–15 to 43–17.
Carlin, B. *Ultrasonics*. N.Y., McGraw–Hill Book Company, Inc., 1949. pp. 4–5, 40–41.

*Primary Examiner*—Christine K. Oda
*Attorney, Agent, or Firm*—Antonelli, Terry, Stout & Kraus, LLP

[57] ABSTRACT

A process for on-line assessment of resistance weldings uses an ultrasonic source which impinges shear waves onto the weld region and an ultrasound receiver. The time at which the melting point of the weld material is reached and a weld nugget begins to form is determined from the output signal of the ultrasound receiver. The volume V of the weld nugget is calculated during the welding operation from the diminishment of shear waves after having reached the melting temperature.

36 Claims, 3 Drawing Sheets

FIG. 1.1
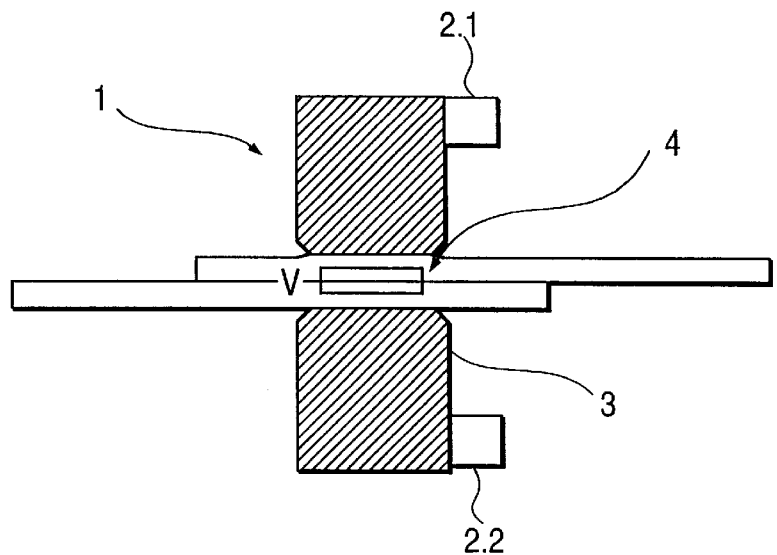
FIG. 1.2
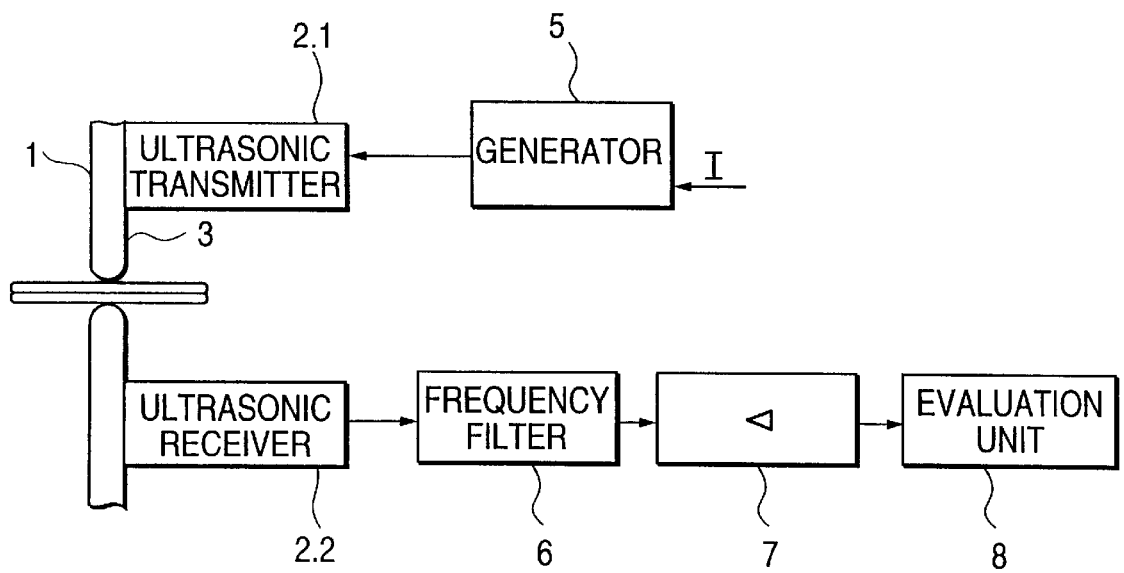

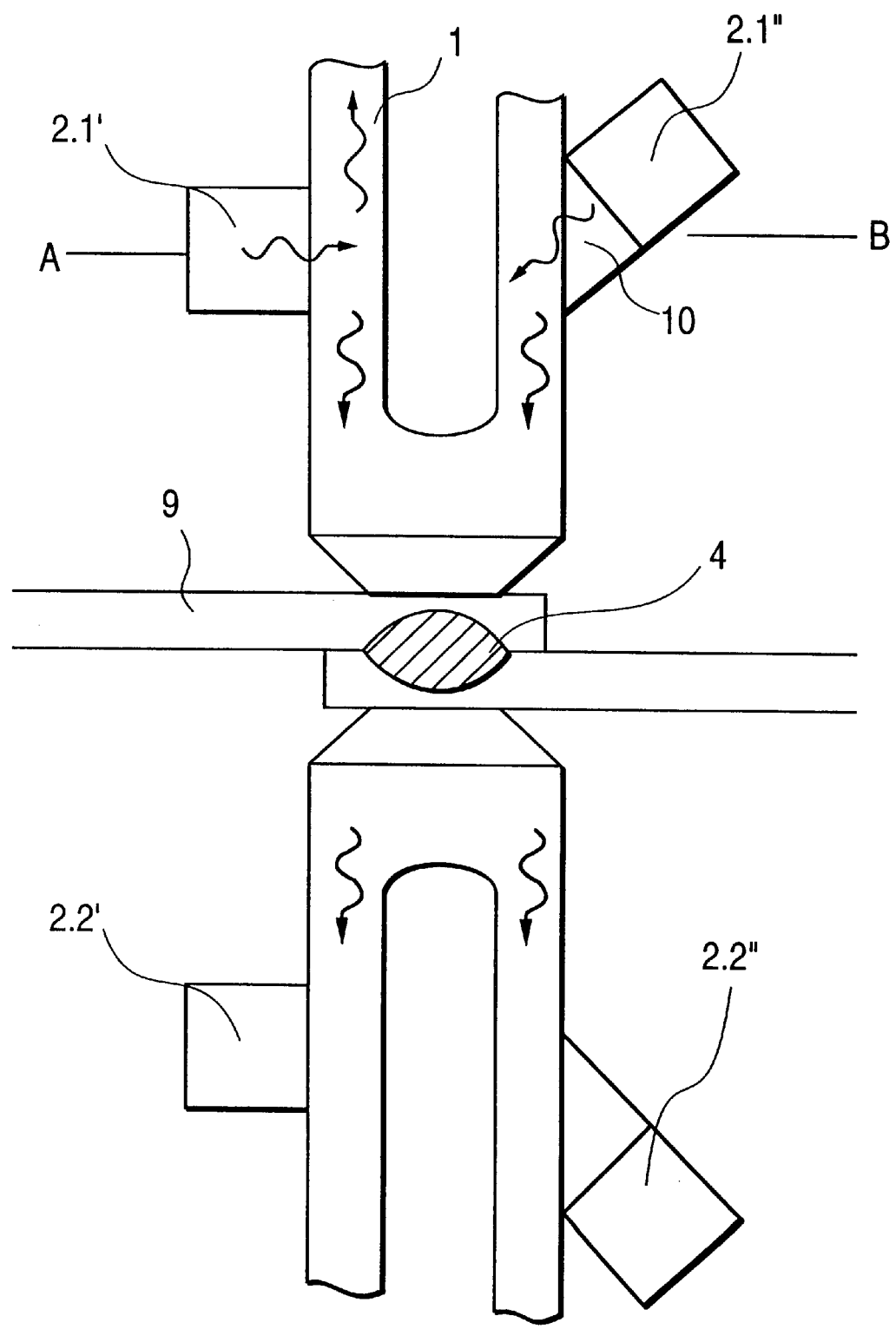
FIG. 2.1

FIG. 2.2
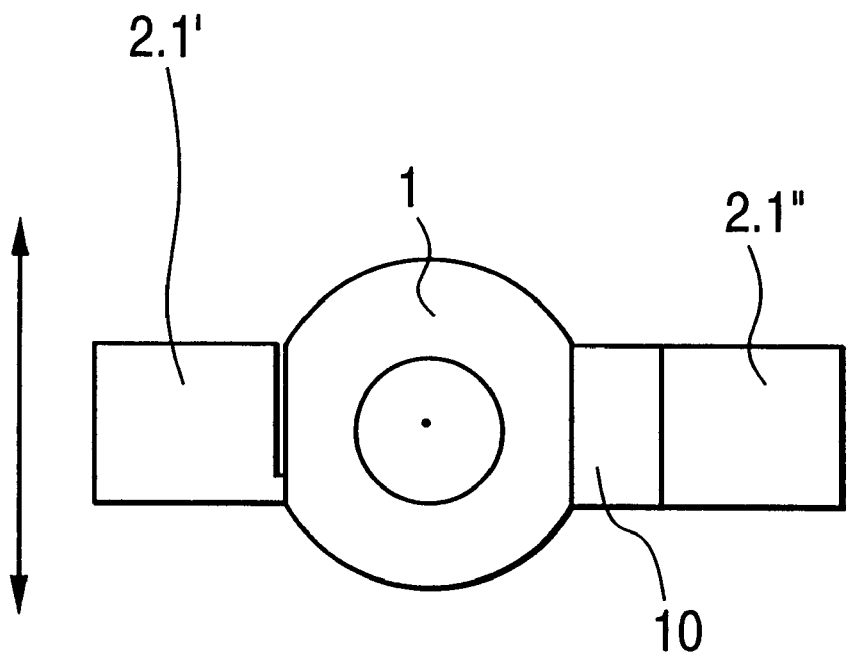
POLARIZATION DIRECTION
OF TRANSVERSE WAVES

PROCESS FOR ASSESSING WELDED JOINTS

DESCRIPTIONS

1. Technical Field

The present invention relates to a process for assessing welding operations and, in particular, resistance welding using an ultrasonic source, which impinges ultrasonic waves onto the weld region and using an ultrasound receiver.

The invented process is not only applicable in resistance welding, but also in a variety of very different welding operations, such as laser welding, gas welding, etc.

2. State of the Art

"Materials Evaluation" No. 47 of August 1989, pages 935–943 describes a process in which the weld region, respectively the weld spot, are sonically inspected during the entire resistance welding process.

The resistance welding process is made up of, i.a., three phases. The first phase is the so-called prepress period. During this period, there is no current flowing. The electrodes close, raising in this way the electrode power of 1–3 KN. Then follows the current flow phase during which the sheets are heated. The post-press period or cooling phase follows the current flow phase. In this phase, the weld nugget cools. It is not until then that the weld electrodes open. All three phases are usually of the same length.

The ultrasonic inspection occurs in the aforementioned method using a longitudinal ultrasonic transmitter in the frequency range of 2 MHz which is disposed within the weld electrodes on the electrode bottom. The ultrasonic inspection starts during the prepress period, in which there is no current flowing, and lasts until the end of the post-press phase. In particular, the ultrasonic transmissivity of the weld spot is assessed during the post-press phase, with the duration of the cooling being determined until attainment of the minimum ultrasonic transmissivity and being correlated with the volume of the molten weld nuggets.

Minimum ultrasonic transmissivity occurs, according to the opinion expounded in this article, at the point of conversion of the iron from the austenitic state to the ferritic state (Curie point) as a consequence of raised ultrasonic absorption at this point of conversion.

A drawback of this process is, however, that the welding process is already terminated and the molten weld nugget cooled when the weld nugget assessment is carried out. The welding process can no longer be influenced. A welding that was detected to be faulty can, however, at most be rewelded.

An apparatus for monitoring a resistance spot welding operation, in which the weld spot is ultrasonically inspected from the inner electrode bottom when the current is flowing with the ultrasonic signal reflected at the opposite electrode being received and evaluated, is known from DE-AS 26 55 415.

This printed publication says nothing about the type of wave that was used; however, the course of the ultrasonic transmissivity depends essentially on the type of wave that was used so that the assumption that the sonic transmissivity of the weld spot during the welding operation first attains a relative maximum, then drops to a minimum and in the further course rises once more to a second maximum cannot be followed.

The first maximum of the ultrasonic transmissivity is explained by the rise in temperature in the sheets to be welded improving the ultrasonic contact between the electrodes and the sheet as well as between the sheets. The subsequent minimum is supposed to result from the fact that the weld material melts. The molten iron raises ultrasonic absorption and reduces sonic transmissivity. The rise in ultrasonic transmissivity during the further course of the welding operation is not explained although this rise, which was not understood prior to the present invention being an element thereof, is essential for the assessment of the welding operation. The assessment process determines the extent of the renewed rise of the ultrasonic transmissivity. The size of the weld nugget is determined from this measured value. The physical explanation for this principle is contradictory in itself. The process is based on the measurement of the difference between two ultrasonic transmissivity values.

The method proposed in "Materials Evaluation" No. 15 of October 1967, pages 226–230 also works with ultrasonic sensors, which generate high-frequency longitudinal ultrasonic signals in the frequency range of 2 MHz with which the ultrasonic inspection of the weld spots is carried out.

In the authors' opinion, however, a weld spot cannot be assessed when it is being ultrasonically inspected at least not during the cooling phase. The authors of this article explain this by a gap being formed between the weld electrodes and the sheets to be welded. When the weld nugget solidifies, the material shrinks forming a gap between the electrode and the sheet, which diminishes ultrasonic transmissivity.

Furthermore, only the amount of thermal charge into the weld spot can be concluded from the course of the ultrasonic transmissivity prior to, during and following welding.

In the proposed process, therefore, the course of the ultrasonic transmissivity of the entire welding operation from the prepress period until and including the cooling phase is compared with a prescribed pattern course. However, the process does not analyse the behavior of ultrasonic transmissivity during the current flow period.

Materialprüfung 32 (1990) 10, pages 311–312, presents examination results for ultrasonic inspection of spot welding: in these examinations, the sonic transmissivity during the prepress period prior to the start of the current flow is compared with the ultrasonic transmissivity during the post-press period following termination of the current flow.

The diminishment in the ultrasonic transmissivity of the weld nugget during the cooling phase compared to the ultrasonic transmissivity prior to welding is explained with the formation of a gap between the electrode and the sheet. The opinion is that due to this gap formation it is principally impossible to recognize adhesive weldings between the weld electrodes and the sheets to be welded by ultrasonically inspecting the weld spots.

The technical activity described in the state of the art is restricted to a comparison of the ultrasonic transmissivity of the weld spot prior to and following the current flow phase. The ultrasonic transmissivity during the current flow phase is not analysed.

DESCRIPTION OF THE INVENTION

The object of the present invention is to provide a process for assessing welding operations and, in particular, resistance welded joints using an ultrasonic source which impinges ultrasonic waves onto the weld region and using an ultrasound receiver which permits online assessment of the quality of the parameters relevant to the welding during the welding operation in order to assess the welded joint, and that, in particular, supplies information about the welding operation during the period during which there is a molten region.

Furthermore, an element of the present invention is to provide an arrangement which permits displacing the ultrasonic sensor away from the electrode bottom during the analysis of the resistance welded joints.

A solution to this object in accordance with the present invention with its further improvements is set forth in the claims hereto.

The present invention is based on the fundamental idea of utilizing the temperature dependency of the ultrasonic transmissivity of the weld nugget, respectively the weld spot during the current flow phase for assessing the weld spot.

In all the state of the art proposals with the exception of the apparatus described in DE-AS 26 55 415, the ultrasonic transmissivity of the weld spot is not analysed during the current flow phase.

The assessment of the ultrasonic transmissivity of the weld spot during the current flow phase is limited, however, in DE-AS 26 55 415 to the determination of the difference of two amplitude values: the difference between the ultrasonic transmissivity at the termination of the current flow phase and the minimal value of the ultrasonic transmissivity during the current flow phase. A physical explanation for this operation is not given. The assessment process itself contradicts the teachings of the present invention concerning the temperature dependency of the ultrasonic transmissivity of the weld spots for transverse respectively torsion waves.

Noteably, the essential reasons for the temperature dependency of the ultrasonic transmissivity of the weld spots have not hitherto been recognized. This is made more apparent in the following:

Various causes of the change in the ultrasonic transmissivity during the individual phases of the welding process are discussed in the aforementioned printed publications. By way of illustration, an increased sonic attenuation is assumed at the Curie temperature or at the melting point. In addition, gap formation between the weld electrodes and the sheets is held responsible for the ultrasonic attenuation during the cooling phase.

Contrary thereto, the present invention is based on being able to describe the sonic inspection of the weld spots, by way of illustration from the weld electrodes, in an exemplary manner as an ultrasonic inspection through a plane-parallel plate, with the electrodes playing the role of the sound-discharging, respectively sound-diverting medium and the weld material playing the role of the sonically inspected plate. This model concept also applies accordingly modified for other welding processes, such as, by way of example laser welding, with which the present invention can also be employed.

Expanding on this fundamental idea of the present invention, two methods of proceeding, which can be utilized alternatively and/or cumulatively, are proposed in accordance with the present invention. In the event of cumulative use, the results obtained with the first method of proceeding can be controlled with the results obtained with the second method of proceeding:

In the first method of proceeding, an element of the present invention is that it is assumed that the ultrasonic transmissivity of the weld material is determined during the consolidated phase, i.e. prior to reaching the melting point, by the temperature dependency of the sonic resistance of the weld material. The course of the temperature in the weld spot is ascertained from this temperature dependency. The diameter of the (presumably attained) weld nugget is calculated during the welding operation from the temperature course and the melting point.

According to the present invention, the sonic velocity $c_2(t)$ in the weld spot is determined from the values of the sonic transmissivity $D(t)$ measured during the welding. The utilized equations (3) and (4) are approximation equations (in the event of plane-parallel plates) which are dependent on the application and, therefore, may also be replaced by other approximations.

$$D(t)=1/\{1+\tfrac{1}{4}*[m(t)-1/m(t)]^2*\sin^2(2*\pi*d/\lambda)\} \quad (3)$$

with $$m(t)=Z_1/Z_2 \text{ and} \quad (2)$$

$$Z_1=\sigma_1*c_1(t) \quad (1)$$

$$Z_2=\sigma_2*c_2(t)$$

In the equations (1) to (3) the following being:
$Z_1$ the sonic resistance of the electrodes,
$Z_2$ the sonic resistance of the weld nugget,
m the ratio of sonic resistances $Z_1/Z_2$,
D the ultrasonic transmissivity factor,
$\sigma_1$ the density of the weld electrodes,
$\sigma_2$ the density of the weld material,
$c_1$ the sonic velocity of the electrode material,
$c_2$ the sonic velocity of the weld material,
d the thickness of the weld nugget,
$\lambda$ ultrasonic wavelength.

Equation (3) yields by implementation of equations (1) and (2) and transformation:

$$c_2(t) = (\sigma_1*c_1/\sigma_2)*1 \Big/ \sqrt{\left(1+(\sigma_1*c_1/\sigma_2)\sqrt{(1/D(t)-1)}\right)/\pi*d*f} \quad (4)$$

In the equation (4) f stands for the ultrasonic frequency.

Based on the consideration that a temperature $T(t)$ can be allocated in the weld spot for each sonic transmissivity value $D(t)$, an element of the present invention is to determine the course of the temperature in the weld spot ($T(t)$) as the function of the duration of the welding operation. A part of the present invention, therefore, is a process for measuring the temperature under difficult conditions like those, by way of illustration, present in welding operations:

For this purpose, the sonic velocity $c_2(t)$ in the weld spot is compared with a given temperature dependency of the sonic velocity $c_2(T)$, and in this way the respective temperature is determined.

In the further course of the process, the melting time $t_s$ in the weld spot is determined from the ascertained course of the temperature in the weld spot by comparing the actual temperature value $T(t)$ with the melting point $T_s$ of the weld material.

The ascertained melting time $t_s$ marks the start of the molten weld nugget formation, with the energy supplied from this time on serving for the weld nugget formation.

Based on theoretical considerations, a relationship according to equation (5) is inferred for the relationship between the square of the diameter of the weld nugget $\phi^2$ and the melting time $t_s$ $$\phi^2=\phi_e^2*2*T_s*B*c_s*(t-t_s)/(c_v*(\exp(B*t_s)-1)) \quad (5)$$

In equation (5) the following being:
$\phi$ the diameter of the weld nugget,
$\phi_e$ the diameter of the electrodes,
$T_s$ the melting point of the weld material,
$c_s$ the specific melting heat of the weld material,
$c_v$ the specific heat of the weld material, $t_s$ the melting time,
t the overall duration of the welding operation.

B is the constant of equation (6) further below.

The diameter of the weld nugget o to be expected at the end of the duration of the welding operation (t) can be determined from equation (5) directly following ascertaining the melting time $t_s$ and still during the welding operation. In this way, the welding result can be principally influenced in a regulating manner during the welding operation, in particular, by altering the intensity of the current I or the duration (t) of the welding operation.

A functional relationship according to equation (6) can be assumed for the temporal course of the temperature T(t) in the weld material.

$$T(t)=A*(1-\exp-(B*t)) \quad (6)$$

With the constants A and B standing for the relationships $$A=J^2*R_0*d/k \quad (7)$$

$$B=k/(c_v*\sigma*d) \quad (8)$$

In equations (7) and (8) the following being:
J the density of the current flowing through the weld spot,
$R_o$ the specific electric resistance of the weld material,
d the thickness of the sheet,
k the thermal conduction coefficient of the arrangement sheet/electrode,
σ the density of the weld material,
$c_v$ the specific heat of the weld material.

Equations (7) and (8) yield for the density of the current:

$$J^2=A*B*c_v*\sigma/d \quad (11)$$

This infers that the density of the current flowing through the weld spot is directly proportional to the product of constant A and B. The proportional constants are known material constants, which if need be can be experimentally determined.

The to-be-determined real course of the temperature T(t) in the weld nugget is approximated by equation (6), with the constants A and B in equation (6), by way of illustration, being determined by means of a "best fit" process.

By utilizing equation (6) and the constants A and B ascertained in this manner, a "best-fit melting time" $t_s$ can be determined. This "best-fit" melting time $t_s$ is largely independent of coincidental measurement fluctuations of the ultrasonic transmissivity D.

In order to ascertain the absolute size of the weld nugget, the diameter $\phi_e$ of the electrode can be determined according to equation (12) when measuring the intensity of the current I.

$$\phi^2_e=I^2*R_o/(A*B*c_v*\sigma) \quad (12)$$

In equation (12) the following being:
I the effective value of the intensity of the current
A and B the constants from equation (6),
$R_o$ the specific electric resistance of the weld material,
$c_v$ the specific heat of the weld material,
σ the density of the weld material.

In the second method of proceeding, an element of the present invention is the utilization of the fact that shear waves, such as transverse waves or torsion waves, are unable to propagate respectively propagate poorly. The ultrasonic attenuation of these waves is determined after having reached the melting point by the size of the volume of the melting weld nugget. The size of the diameter of the weld nugget is determined directly from the value of the ultrasonic attenuation following having reached the melting point in the weld spot.

Therefore, according to the present invention the time point $t_s$ at which the melting point $T_s$ of the weld material is reached is determined from the output signal of the ultrasound receiver and the molten weld nugget begins to form.

In this manner, the volume V of the weld nugget can be calculated, in particular, from the attenuation of the shear waves after having reached the melting point.

The current volume V of the weld nugget can be determined for the time $t>t_s$ via the following relationship:

$$V=B'*(D(t)-D(t_s))+C' \quad (12')$$

with the following being:
B', C' experimentally determined constants
D(t) the ultrasonic transmissivity at the time t
$D(t_s)$ the ultrasonic transmissivity upon reaching the melting point.

As an alternative or in addition, the volume V of the weld nugget reached at the termination of the welding can be determined from the period Δt from the melting time to the termination of the welding operation via the following relationship:

$$V=B''*\Delta t+C'', \quad (13)$$

with B'' and C'' also being constants to be experimentally determined.

In another possible method, the attainable volume of the weld nugget during the period at from reaching the melting point to the termination of welding is determined via the following relationship:

$$V=B'''(\Delta t+D(t_s)/([D(t_s+\delta t)-D(t_s)]/\delta t))+C''' \quad (14)$$

with

B''', C''' experimentally determined constants
$D(t_s)$ the ultrasonic transmissivity upon reaching the melting temperature, and
δt "the time differential", i.e. a small time interval.

Furthermore, for the determination of the sonic transmissivity D(t) of the weld region during each current halfwave of the weld current from the output signal A(t) from the ultrasound receiver within a first time window i which is delayed in contrast to the ultrasonic transmission signal, the transmission level of which is held constant, by a defined delay period, the average ultrasonic energy $E_{1i}$ an be determined according to the following equation:

$$E_{1i} = 1/\Delta t_1 \int_O^{\Delta t_1} A(t)^2 dt. \quad (15)$$

Within a second time window which lies prior to or following the first time window and during which no ultrasonic waves are impinged on the weld material, the average sound emission energy $E_{2j}$ resulting from the welding process can be determined according to the following equation $$E_{2j} = 1/\Delta t_2 \int_O^{\Delta t_2} A(t)^2 dt. \quad (16)$$

An alternative thereto is the following method of proceeding according to which the ultrasonic value $E_{1i}$ is determined from the maximum output signal A(t) occurring within this time window for the determination of the sonic transmissivity D(t) of the weld region during each current halfwave of the welding current from the output signal A(t) from the ultrasound receiver within a first time window i which is delayed by a defined delay time in contrast to the ultrasonic transmission signal the transmission level of which is held constant. Within a second time window which lies prior to or following the first time window and during which the weld material is not impinged with ultrasonic waves, the sound emission value $E_{2j}$ occurring due to the welding process is determined from the maximum output signal A(t) occurring within the second time window.

This method of proceeding permits correcting specific measured values for the ultrasonic transmissivity D if the continuously determined sound emission level $E_{2j}$ exceeds a preset threshold value. The correction may occur by replacing the disturbed sonic transmissivity $E_{1i}$ by the average value of both adjacent values.

In the invented arrangement for utilizing ultrasound in the analysis of resistance welded joints, the weld spot is sonically inspected during the welding operation: the ultrasonic signals are transmitted, by way of illustration, in one of the weld electrodes; the ultrasonic signals are received following the sonic inspection of the weld spot, respectively the welded region by a receiver, the output signals of which an assessment and control unit evaluates for the assessment and, if need be, for the regulation of the welding process.

The state of the art solely describes processes for assessing spot welding with the aid of ultrasonic analysis in which the weld spot is sonically inspected from one of the inner weld electrode bottoms by the ultrasonic pulses in the form of high-frequency longitudinal waves. In contrast thereto, the arrangement of the ultrasonic transmitter and, if need be, the ultrasound receiver according to the present invention occurs at the outside wall of the electrode shank or the electrode holder of an electrode.

However, a prerequisite therefor is that the sound waves generated and utilized for the sonic inspection possess good propagation behavior in the electrode wall. This is made possible by not using longitudinal waves for the sonic inspection of the weld nugget, but rather shear waves and, in particular transverse waves or torsion waves. The ultrasonic activating occurs in such a manner that a transverse or torsion wave is generated in the electrode wall, by way of illustration, with an electrosonic ultrasonic transducer.

The actual embodiment is carried in such a manner that an ultrasonic transmitter is disposed at the outside wall of the electrode shank or of the electrode holder of one of the electrodes of the welder and analogous thereto the outside wall of the other weld electrode is provided with an ultrasound receiver.

In the event an ultrasonic transducer is utilized which can work during transmission and reception operation, this ultrasonic sensory mechanism is only attached to the outside wall of the electrode shank or electrode holder of one electrode.

The transverse or torsion waves utilized for the sonic inspection lie preferably in the frequency range of 50 to 500 kHz.

The operation range can, however, amount to up to 1 MHz.

For transmitting the horizontally polarized transverse waves into the electrode wall, it is essential that the polarization vector runs perpendicular to the axis of the tube of the electrodes.

BRIEF DESCRIPTION OF THE DRAWING

The present invention is made more apparent in the following using preferred embodiments with reference to the accompanying drawing wherein:

FIGS. 1.1 and 1.2 are schematic representations of the electrode configuration of a spot welder, FIGS. 2.1 and 2.2 are schematic representations of the course of a transverse wave in the electrode wall of an electrode.

DESCRIPTION OF PREFERRED EMBODIMENTS

In the invented process, the velocity $c_2(t)$ in the weld spot is determined from the values for the sonic transmissivity D(t) measured during the welding operation.

The following approximation equations which hold for the application "acoustic passage through a plane-parallel plate" can be utilized for resistance welding of sheets.

In other configurations and/or weld processes, the approximation equations are to be changed according to the respective application:

$$D(t)=1/\{1+\tfrac{1}{4}*[m(t)-1/m(t)]^2*\sin^2(2*\pi*d/\lambda)\} \quad (3)$$

with $$m(t)=Z_1/Z_2 \text{ and} \quad (2)$$

$$Z_1=\sigma_1*c_1(t) \quad (1)$$

$$Z_2=\sigma_2*c_2(t)$$

In the equation (1)–(3) the following being:
$Z_1$ the sonic resistance of the electrodes,
$Z_2$ the sonic resistance of the weld nugget,
m the ratio of sonic resistances $Z_1/Z_2$,
D the ultrasonic transmissivity factor,
$\sigma_1$ the density of the weld electrodes,
$\sigma_2$ the density of the weld material,
$c_1$ the sonic velocity of the electrode material,
$c_2$ the sonic velocity of the weld material,
d the thickness of the weld nugget,
$\lambda$ ultrasonic wavelength.

From equation (3) it is seen that the transmissivity factor D depends on the relationship m of the sonic resistances of electrode $Z_1$ and the sonic resistance $Z_2$ of the weld material. The sonic resistances of weld electrode $Z_1$ and the weld material $Z_2$ are yielded according to equation (1) by approximation from the product of density $\sigma$ and the sonic velocity c in the respective medium.

The present invention is based on changes of the ultrasonic transmissivity of the weld spot are caused by temperature dependent changes of the sonic velocity $c_2$ in the weld spot and in that when there is a change in the sonic velocity $c_2$ in the weld spot according to equation (1) the sonic resistance $Z_2$ of the weld spot changes whereas the sonic resistance of the electrodes $Z_1$ remains constant. In this way, the relationship of the sonic resistances m changes and according to equation (3) the transmissivity factor D. The term with $\sin^2(2*\pi*d/\lambda)$ should be considered constant in the following and initially not be taken into consideration.

If it is assumed that the weld electrodes are made of copper and the sheets to be welded are made of iron, at the beginning of the current flow phase (at room temperature), the sonic resistance in the copper ($Z_1$=20.1) is less than the sonic resistance in iron ($Z_2$=25.3). Therefore, at the beginning of the welding operation according to equation (3), the transmissivity factor D is: D<1.

The sonic velocity in the iron drops during welding due to the rise in temperature and, therefore, the sonic resistance $Z_2$ as well. The sonic transmissivity D, being temperature dependent, reaches according to equation (3) first a maximum, noteably at the time t in which the sonic resistance of iron $Z_2$ assumes the value of the sonic resistance of the weld electrodes $Z_1$; in this event, m=1 and according to equation (3) the transmissivity D of the weld spot is then maximum, i.e., D=1.

In the event of a further rise in temperature, the sonic resistance of the iron continues to fall and therefore the transmissivity factor D also begins to diminish again. The sonic transmissivity of the weld spot is determined by equation (3) until the melting point is reached. Upon reaching the melting point, the sonic transmissivity is further reduced, now however due to the great sonic attenuation of the shear waves in liquid media. The degree of attenuation of the transverse waves depends directly on the size of the molten volume following having reached the melting point $T_s$, with the already described relationships being valid.

A renewed rise in ultrasonic transmissivity is, therefore, in contradiction to the assertions in the state of the art (DE-AS 26 55 415) not a sign of a good welding, but rather is a sign of disturbances in the welding process. In particular, the assertions in the state of the art do not relate to shear waves.

In spot welding processes it happens that the molten weld material, e.g., is pressed out of the weld nugget due to spatter formation or too little electrode pressure during the welding operation. In this case, the weld nugget loses liquid weld material including the heat energy stored therein. This effect is noticeable by a renewed rise in the transmissivity factor D.

Based on the relationship between the ultrasonic transmissivity D and the sonic resistance $Z_2$ in the weld spot, the relationship between the sonic velocity $c_2$ in the weld spot and the transmissivity factor D of the weld spot given in equation (4) can be derived from equation (3).

$$c_2(t) = (\sigma_1 * c_1 / \sigma_2) * 1 \bigg/ \sqrt{\left(1 + (\sigma_1 * c / \sigma_2)\sqrt{(1/D(t) - 1)}\right) / \pi * d * f} \quad (4)$$

In equation (4) f stands for the ultrasonic frequency.

Therefore, with the aid of equation (4) the sonic velocity $c_2(t)$ in the weld material is allocated to the transmissivity factor D(t). The invented process, therefore, permits determining the course of the temperature in the weld spot T(t) as the function of the duration of the welding operation, with the sonic velocity $c_2(t)$ in the weld spot being compared with a preset temperature dependency of the sonic velocity $c_2(T)$.

This occurs due to the fact that the determined sonic velocity $c_2(t)$ is compared with a preset temperature dependency of the sonic velocity $c_2(T)$ in the weld material. In this preferred embodiment, the following assumed linear relationship is utilized exemplarily for the temperature dependency of the sonic velocity in the weld material.

$$T(t)=(c_{2o}-c_2(t))*T_s/c_2 \quad (4')$$

In this equation the following being
$c_{2o}$ the sonic velocity of the weld material at room temperature,
$T_s$ the melting point of the weld material and
$c_2$ the difference in the sonic velocities between the room temperature and the melting point.

The relationship may be replaced for the respective application by an experimentally or theoretically determined temperature dependency of the sonic velocity.

Furthermore, the melting time $t_s$ of the weld material is determined from the ascertained course of the temperature T(t) in the weld spot by comparing the melting point of the iron $T_s$. The ascertained melting time $t_s$ marks the beginning of weld nugget formation.

The ascertained melting time $t_s$ marks the start of weld nugget formation, with the energy supplied following this time being utilized for weld nugget formation.

A functional relationship according to equation (5) may be assumed for the temporal course of the temperature T(t) in the weld material.

$$T(t)=A*[1-\exp-(B*t)] \quad (5)$$

With the constants A and B standing for the relationships $$A=J^2*R_o*d/k \quad (6)$$

$$B=k/(c_v*\sigma*d) \quad (7)$$

In equations (6) and (7) the following being:
J the density of the current flowing through the weld spot,
$R_o$ the specific electric resistance of the weld materials,
d the thickness of the sheet,
k the thermal conduction coefficient of the arrangement sheet/electrode,
$\sigma$ the density of the weld material,
$c_v$ the specific heat of the weld material.

Equations (6) and (7) yield the following relationship for the density of the current:

$$J^2=A*B*c_v\sigma/d \quad (8)$$

This infers that the density of the current flowing through the weld spot is directly proportional to the product of constant A and B. The proportional constants are known material constants.

The diameter $\sigma_e$ of the electrode according to equation (9) may be determined during measurement of the current intensity I in order to ascertain the absolute size of the weld nugget.

$$\phi^2_e=I^2*R_o/(A*B*c_v*\sigma) \quad (9)$$

In equation (9) the following being:
I the effective value of the intensity of the current
A and B the constants from equation (5),
$R_o$ the specific electric resistance of the weld material,
$c_v$ the specific heat of the weld material,
$\sigma$ the density of the weld material.

By using a preset temperature dependency of the sonic velocity, e.g., according to equation (4'), a temperature value in the weld nugget can be alloted for each transmissivity value D according to equation (4). When an initial minimum in the sonic transmissivity of the weld spot has been reached, a renewed rise in the ultrasonic transmissivity means a drop in the temperature in the weld spot. If the temperature in the weld spot drops below a preset threshold value, e.g., the melting point, during the current flow phase, this is a sign that there is a disturbance in the welding process and is indicated.

Indication occurs if a second relative maximum of the ultrasonic transmissivity is reached, and this transmissivity maximum exceeds a preset peak value.

Moreover, correction of the diameter of the weld nugget can occur continuously. If a disturbance is indicated in such a manner that the temperature of the weld nugget for the time period $t_3$ drops below the melting point, the conducted process for determining the diameter of the weld nugget has to be modified in such a manner that in order to calculate the diameter of the weld nugget according to equation (13), the time period $t_3$ during which the temperature remains below the melting point is subtracted from the over all duration of the welding operation t.

$$\phi = \phi_e{}^*(-K_1 + (Dt_{min})/D'_m - t_{min}) + K_2) \quad (11)$$

$K_1$, $K_2$ constants, which have to be determined by means of sample weldings, $D(t_{min})$ is the value of the normed ultrasonic transmissivity at the time of the minimum of the derivation.

The preceding embodiments show that the course of the ultrasonic permissivity factors in a weld spot are determined as the function of the duration of the welding operation by the course of the temperature in the weld spot. This is the case until the melting point is reached in the weld material. Following this, the ultrasonic permissivity factor is determined by the size of the volume of the molten weld nugget. If the materials of the weld electrodes and of the weld materials are known and the temperature dependency of the sonic velocity is known, a course pattern of the ultrasonic permissivity factor can be calculated in advance for each weld current intensity as the function of the duration of the welding operation or experimentally traced within the scope of sample weldings.

This course pattern fixes the course of the temperature in the weld spot and the size of the weld nugget. By way of illustration, the maximum transmissivity and the melting point have to be reached according to preset times.

In practice, control of the welding process is desired in addition to assessment of the weld spots in order to prevent poor weldings. The control of the welding process may occur in such a manner that the course of the ultrasonic transmissivity is compared with a prescribed course pattern (desired value). In the event of deviations from the course pattern, the welding parameters, e.g., the current intensity are changed accordingly until the following transmissivity values coincide again with the course pattern.

Measurement of the sound emission in a second measurement window, which lies, e.g., directly prior to the transmission times, serves the purpose of detecting disturbances, e.g., due to spatter formation, in the determination of the ultrasonic transmissivity values. If disturbance signals are detected in one of the second measurement windows, the following measured value is corrected according to the influence of the disturbance or is replaced by the average value of the measured values prior to and following the disturbance.

The selection and the arrangement of the ultrasonic transmitter or transmitters and of the ultrasound receiver or receivers occurs according to the respective application. If need be, one and the same sensor may be utilized as the ultrasonic transmitter and ultrasound receiver.

Furthermore, ultrasonic waves may also be activated with laser beams.

Therefore, in the following a possible realization of the invented process is only described by way of example:

FIG. 1.1 shows a schematic representation of a preferred embodiment of the invention having sensory mechanisms disposed on the weld electrodes. The electrodes 1 of the welder are provided with ultrasonic transducers. An electrode of the welder is provided with an ultrasonic transmitter 2.1. In the second electrode is a receiving probe 2.2, e.g., a piezoelectric ultrasonic transducer.

The ultrasonic transmitter 2.1 and the receiver 2.2 are disposed on the outside wall of the respective electrode shank 3. The sonic inspection of the weld nugget 4 occurs from the transmission probe 2.1 by means of horizontal polarized transverse waves.

With the start of the weld current, a generator 5 which emits an electric burst signal to the transmission probe 2.1 following a settable delay period is activated at the beginning of each current halfwave. This generates in the weld electrode 1 an ultrasonic signal which propagates via the electrode through the weld spot, respectively the weld nugget 4 to the second electrode. This signal is received with the receiving probe 2.2 at the second electrode. FIG. 1.2 depicts a block diagram of the arrangement.

The reception signal is filtered narrow-band by means of a frequency filter 6 to the frequency spectrum of the transmission signal and amplified by approximately 40 dB in a subsequent amplifier 7. In the evaluation unit 8 connected thereafter, the ultrasonic signals are recorded and analyzed. Evaluation unit 8 may be employed as a control respectively regulating unit for the welding process.

FIG. 2 shows various possible ways of coupling in and the course of a horizontal polarized transverse wave in the wall of a tube electrode 1. FIG. 2.1 shows a longitudinal section and FIG. 2.2 a cross-section in the A-B line in FIG. 2.1.

The wave activated by an electro-acoustic ultrasonic transducer 2.1' which is disposed at an angle of 90° to the tube axis arrives at a frequency of, by way of illustration, 100 KHz in the to-be-evaluated weld nugget 4 which forms between the sheets 9. The utilized wavelength $\lambda$ is selected in such a manner that $\lambda/2$ corresponds approximately to the diameter of the electrode 1, respectively the resulting weld nugget 4.

In order to improve the coupling in of the ultrasound the sonic irradiation of transverse ultrasonic waves may also occur by means of an ultrasonic transducer 2.1" at an angle of, e.g., 45°, cf. FIG. 2.1. (right side). The elbow 10 is also made of copper. In this case, the entire ultrasonic energy goes into the bottom part of electrode 1. On the other hand, during the perpendicular sonic irradiation only approximately 50% of the transmission signal reaches into the bottom part of the electrode, the other half propagates in the opposite direction, cf. FIG. 2.1 (left side). The optimum polarization direction of the transverse waves is given in FIG. 2.2.

The acoustically irradiated signals are reflected according to their irradiation angle at the electrode walls and propagate in a "zick-zack" manner in the electrode wall by repeated reflection. In the described polarization direction (horizontal to the electrode surface) there is no conversion into other types of waves in the case of reflections at the electrode wall. These types of waves generated in the electrode wall are referred to in the trade literature as "SH-wave" (shear horizontal).

The use of this type of wave is advantageous for the sonic inspection of electrodes and the weld nugget in order to obtain a high degree of efficiency.

Moreover, corresponding assemblies of the ultrasound receivers 2.2'. (right angle) and 2.2" (45° angle) are depicted in FIG. 2.1.

What is claimed is:

1. A process for on-line assessment of welding operations using an ultrasonic source which impinges shear waves onto the weld region and using an ultrasound receiver, employing the following steps:

determining the time $t_s$ at which the melting temperature $T_s$ of the weld material is reached and a weld nugget begins to form from the output signal of the ultrasound receiver, calculating the volume V of the weld nugget during the welding operation from the diminishment of the shear waves after having reached the melting temperature $T_s$, wherein the step of calculating determines said volume V of the weld nugget attained at the termination of the welding operation from the time period $\Delta t$ of the melting time to the termination of the welding operation via the following relationship:

$$V=B'''*\Delta t+C''$$

with B" and C" also being constants to be experimentally determined.

2. A process according to claim 1, wherein the current volume V of the weld nugget at the time $t>t_s$ is determined via the following relationship:

$$V=B'*(D(t)-D(t_s))+C'$$

with the following being:
B', C' experimentally determined constants
D(t) the ultrasonic transmissitivity at said time t
$D(t_s)$ the ultrasonic transmissivity upon reaching the melting temperature $T_s$.

3. A process according to claim 1, wherein the step of calculating determines said volume of the weld nugget attained during a time period $\Delta t$ from reaching the melting temperature $T_s$ to the end of the welding operation via the following relationship:

$$V=B'''(\Delta t+D(t_s)/([D(t_s+\sigma t)-D(t_s)]/\sigma t)+C'''$$

with the following being:
B''', C''' experimentally determined constants
$D(t_s)$ the ultrasonic transmissivity upon reaching the melting temperature $T_s$, and
σt "time differential", i.e. small time interval.

4. A process according to claim 1, wherein said step of determining said time $t_s$ at which said melting temperature $T_s$ is reached ascertains the time at which the temporal change of said diminishment of said shear waves changes from a comparatively small to a comparatively large value.

5. A process according to claim 1 further comprising the following steps:
determining a sonic velocity $c_2$ of said shear waves in the weld region as a function of time t,
determining a temperature T(t) of the weld region as a function of the duration of the welding operation from the ascertained sonic velocity $c_2(t)$ in the weld region by comparison with a previously ascertained temperature dependency of said sonic velocity $c_2(t)$ in the weld material, and
determining said melting time $t_s$ of the weld material from said course of the temperature T(t) in the weld region by comparison with said melting temperature $T_s$ of the weld material.

6. A process according to claim 5, comprising the further step of measuring said ultrasonic transmissivity D(t) (ultrasonic transmissivity factor) during the welding operation as a function of the time measured and said current sonic velocity $c_2(t)$ in the weld spot being determined therefrom.

7. A process according to claim 5, wherein said step of determining calculates said ultrasonic velocity $c_2(t)$ from said ultrasonic transmissivity D(t) by means of the following equation:

$$c_2(t) = (\sigma_1 * c_1/\sigma_2)*1/\sqrt{(1+(\sigma_1*c/\sigma_2)*\sqrt{(1/D(t)-1}/\pi*d*f}$$

with the following being:
$\sigma_1$ the density of the weld electrodes, respectively the ultrasonic source,
$\sigma_2$ the density of the weld material,
$c_1$ the sonic velocity of the electrode material respectively of the source material,
$c_2$ the sonic velocity of the weld material,
d the density of the weld nugget,
f the ultrasonic frequency.

8. A process according to claim 7, comprising the following steps in order to determine said sonic transmissivity D(t) of the weld region during each current halfwave of the weld current, from an output signal A(t) from said ultrasound receiver:
determining an average ultrasonic energy $E_{1i}$ within a first time window i, which is delayed by a defined delay time in contrast to said ultrasonic transmission signal the transmission level of which is held constant, according to the following equation, $$E_{1i} = 1/\nabla t_1 \int_O^{\nabla t_1} (A(t))^2 dt.$$

and determining an average sound emission energy $E_{2j}$ resulting from the welding process within a second time window which lies prior to or following said first time window and during which no ultrasonic waves are impinged on the weld material according to the following equation, $$E_{2i} = 1/\nabla t_1 \int_O^{\nabla t_1} (A(t))^2 dt.$$

9. A process according to claim 7, comprising the following steps in order to determine said sonic transmissivity D(t) of the weld region during each current halfwave of the weld current, from an output signal A(t) from said ultrasonic receiver:
determining an ultrasound value $E_{1i}$ within a first time window i, which is delayed by a defined delay time in contrast to said ultrasonic transmission signal the transmission level of which is held constant, from the maximum output signal A(t) occurring within said time window,
and determining a sound emission value $E_{2j}$ resulting from the welding process from the maximum output signal A(t) occurring within said second time window which lies prior to or following said first time window and during which no ultrasonic waves are impinged on the weld material.

10. A process according to claim 8 or 9, by further comprising the step of correcting specific measured values for said ultrasonic transmissivity D if the continuously determined sound emission level $E_{2j}$ exceeds a preset threshold value.

11. A process according to claim 10, wherein said step of correcting is performed by replacing the disturbed sonic transmissivity value $E_{1i}$ with the average value of the two adjacent values.

12. A process according to claim 1, wherein said shear waves are transverse ultrasonic waves or torsion waves.

13. A process according to claim 1, further comprising the step of measuring the current intensity and the current diameter of the electrode being determined from said measured current intensity.

14. A process according to claim 1, further comprising the step of calculating the diameter of the weld nugget to be expected at the termination of the welding period t from the melting time according to the following equation:

$$\sigma^2=\sigma_e^2*2* T_s*B*c_s*(t-t_s)/c_v*(\exp(B*t_s)-1)$$

with the following being:

$\sigma_e$ the diameter of the electrodes,
$c_s$ the specific melting heat of the weld material,
$c_v$ the specific heat of the weld material,
t the overall duration of the welding operation,
$t_s$ the melting time,
and the value of B being empirically determined.

15. A process according to claim 13, comprising the step of determining a value of B as well as a further value A according to a "best-fit" method from the temporal course of the temperature T(t) in the weld material via the following relationship $$T(t)=A*(1-\exp-(B*t)).$$

16. A process according to claim 15, wherein the following relationships standing by approximation for said values of A and B:

$$A=J^2*R_o*d/k$$

$$B=k/(c_v*\sigma*d)$$

with the following being:
J the density of the current
$R_o$ the specific electric resistance of the weld material,
$c_v$, the specific heat of the weld material
σ the density of the weld material,
d the thickness of the weld material,
k the thermal conduction coefficient of the arrangement weld material/electrode,
and the actual current density J in the weld material being determined from the determined values of A and B according to the following equation:

$$J^2=A*B*c_v*/d\sigma.$$

17. A process according to claim 1, wherein the welding results are influenced by changing the current intensity I or said welding period t during welding.

18. A process according to claim 1, wherein a "best-fit" melting time $t_s$, which is largely independent of the coincidental measurement fluctuations of said ultrasonic transmissivity D, is determined by applying the relationship $A=J^2*R_o*d/k$.

19. A process according to claim 1, comprising the step of determining said diameter of the electrode $\sigma_e$ according to equation (12) in order to determine the absolute size σ of the weld nugget when measuring said current intensity I $$\sigma^2_e=I^2*R_o/(A*B*c_v*\sigma) \qquad (12).$$

20. A process according to claim 1, further comprising indication of disturbances in the welding process and indication of a second relative maximum of said ultrasonic transmissivity if said transmissivity maximum exceeds a preset peak value.

21. A process according to claim 4, comprising a further step of, if a disturbance is indicated in such a manner that the temperature of the weld nugget drops below the melting temperature $T_s$ for a time period $t_3$, modifying said process for determining said diameter of the weld nugget in such a manner that in calculating said diameter of said weld nugget said time period $t_3$ is subtracted from the overall duration of the welding operation.

22. A process according to claim 1, wherein the welding operations comprise resistance weldings.

23. An arrangement for utilizing ultrasound in the analysis of resistance welded joints having:

an ultrasonic transmitter which impinges said resistance welded joint with ultrasonic waves, an ultrasound receiver which receives the ultrasonic waves following sonic inspection, said ultrasonic transmitter being attached to the outer electrode shank or to the electrode holder, and generating shear waves and, in particular, transverse or torsion waves for the sonic inspection of the weld spots and an evaluation and control unit which determines a melting time $t_s$ of the weld material in the welding region in accordance with an output of the ultrasonic receiver; and at least one of a diameter ϕ and a volume V of the weld spot during the welding process and, if need be, controls the welding process in accordance with the determination.

24. An arrangement according to claim 23,
characterized by said ultrasound receiver being attached to said outer electrode shank or said electrode holder.

25. An arrangement according to claim 24,
characterized by said ultrasonic transmitter being disposed at the outside wall of said electrode shank or said electrode holder of the one electrode of the welder and said ultrasonic receiver being disposed at the other weld electrode.

26. An arrangement according to claim 23, characterized by an ultrasonic transducer which can be operated in transmission and reception operation being only provided at said outside wall of said electrode shank or holder.

27. An arrangement according to one of the claims 23 to 26, characterized by the transverse or torsion waves activated in the electrode wall with an electro-acoustic ultrasonic transducer lying in the frequency range from 50 to 500 KHz.

28. An arrangement according to claim 23,
characterized by the operation range for the frequency amounting up to 1 MHz.

29. An arrangement according to claim 23,
characterized by polarization vector being aligned perpendicular to the axis of the tube of the electrodes.

30. An arrangement according to claim 23,
characterized by the frequency of said transverse or torsion waves employed for utilizing ultrasound is selected in such a manner that the respective halfwave λ/2 corresponding approximately to the diameter of the weld electrodes, respectively of the weld nugget.

31. An arrangement according to claim 23,
characterized by horizontally polarized transverse waves being irradiated at an angle.

32. An arrangement according to claim 23, wherein the control unit evaluates the output signals of the ultrasound receiver for determining a melting time $t_s$ of the weld material and enables determination of one of a diameter ϕ and a volume V of a weld nugget during a welding operation.

33. A process for assessing welding operations comprising the steps of:

impinging ultrasonic waves onto a weld region and receiving ultrasonic waves utilizing ultrasonic transmitter and receiving means;

determining a melting time $t_s$ of the weld material in the welding region in accordance with an output of the ultrasonic receiving means; and determining at least one of a diameter ϕ and a volume V of a weld nugget during a welding operation.

34. A process for accessing resistance welded joints using an ultrasonic transmitter which impinges ultrasonic waves onto the weld region and using an ultrasound receiver according to claim 33, wherein during the weld operation the sonic velocity $c_2$ of the ultrasonic waves in the weld region is determined as the function of the time t, the temperature T(t) of the weld region is determined by the comparison with a previously ascertained temperature dependency of the sonic velocity $c_2(t)$ in the weld material as the function of the duration of the welding operation from the ascertained sonic velocity $c_2(t)$ in the weld region, the melting time $t_s$ of the weld material is determined from the course of the temperature T(t) in the weld region by comparison with the melting point of the weld material $T_s$, and the diameter $\phi$ of the weld nugget to be expected at the termination of the welding period t is calculated during the welding operation from the melting time $t_s$.

35. A process according to claim 34, characterized by longitudinal ultrasonic waves being employed as ultrasonic waves.

36. A process according to claim 34 or 35, characterized by the ultrasonic transmissivity D(t) (ultrasonic transmissivity factor) being measured during the welding operation as the function of time and the current sonic velocity $c_2(t)$ in the weld spot being determined therefrom.

* * * * *